United States Patent [19]

Desbiendras et al.

[11] Patent Number: 5,348,681

[45] Date of Patent: Sep. 20, 1994

[54] COMPOSITION BASED ON 1,1,1,3,3-PENTAFLUOROBUTANE AND METHYLENE CHLORIDE, FOR THE CLEANING AND/OR DRYING OF SOLID SURFACES

[75] Inventors: Daniel Desbiendras, Villetaneuse; Pascal Michaud, Saint-Gratien, both of France

[73] Assignee: Elf Atochem S.A., Puteaux, France

[21] Appl. No.: 87,099

[22] Filed: Jul. 7, 1993

[30] Foreign Application Priority Data

Aug. 21, 1992 [FR] France .................................. 92 10199

[51] Int. Cl.5 .......................... C11D 7/32; C11D 7/50; C23G 5/028; B08B 3/00
[52] U.S. Cl. ..................................... 252/172; 134/12; 134/31; 134/40; 134/42; 252/153; 252/162; 252/194; 252/364; 252/DIG. 9
[58] Field of Search .............. 252/153, 162, 172, 194, 252/364, DIG. 9; 134/12, 31, 40, 42

[56] References Cited

U.S. PATENT DOCUMENTS

| | | |
|---|---|---|
| 5,099,081 | 3/1992 | Bolmer et al. ................. 570/180 |
| 5,099,082 | 3/1992 | Bolmer et al. ................. 570/180 |
| 5,250,208 | 10/1993 | Merchant et al. ............... 252/67 |
| 5,268,120 | 12/1993 | Michaud ....................... 252/162 |
| 5,268,121 | 12/1993 | Michaud ....................... 252/171 |
| 5,275,669 | 1/1994 | Van der Puy et al. ........... 252/171 |

FOREIGN PATENT DOCUMENTS

| | | |
|---|---|---|
| 432672 | 6/1991 | European Pat. Off. . |
| 2-222495 | 9/1990 | Japan . |
| 5-168805 | 7/1993 | Japan . |
| 5-171190 | 7/1993 | Japan . |
| 09216 | 5/1993 | World Int. Prop. O. . |

Primary Examiner—Linda Skaling
Attorney, Agent, or Firm—Morgan & Finnegan

[57] ABSTRACT

To replace cleaning compositions based on 1,1,2-trichloro-1,2,2-trifluoroethane (F113), the invention provides a composition comprising, by weight, 30 to 70% 1,1,1,3,3-pentafluorobutane (F365-mfc) and 70 to 30% methylene chloride. These two compounds form a positive azeotrope (B.p.=33.6° C. at normal pressure).

The composition, optionally stabilized, can be used for the cleaning and/or the drying of solid surfaces, in particular for removing flux from printed circuits and for degreasing mechanical components.

8 Claims, No Drawings

COMPOSITION BASED ON 1,1,1,3,3-PENTAFLUOROBUTANE AND METHYLENE CHLORIDE, FOR THE CLEANING AND/OR DRYING OF SOLID SURFACES

FIELD OF THE INVENTION

The present invention relates to the field of fluorinated hydrocarbons. More particularly, its subject is a new composition which exhibits an azeotrope and which can be used in the applications of drying, cleaning, degreasing and drycleaning solid surfaces, in particular in the removal of flux and the cold cleaning of printed circuits.

BACKGROUND OF THE INVENTION 1,1,2-Trichloro-1,2,2-trichloroethane (known in the profession under the name F113) is widely used in industry for the cleaning and degreasing of solid surfaces. Besides its application in electronics to the cleaning of solder fluxes in order to remove the surface-attacking flux which adheres to printed circuits, there may be mentioned its applications to the degreasing of heavy-metal components and to the cleaning of mechanical components of high quality and high precision, such as, for example, gyroscopes and military or aerospace equipment. In its various applications, F113 is most often combined with other organic solvents (for example methanol), preferably in the form of azeotropic or pseudoazeotropic mixtures which do not demix and which, used at reflux, have substantially the same composition in the vapor phase as in the liquid phase.

However, F113 is one of the completely halogenated chlorofluorocarbons which are currently suspected of attacking or damaging stratospheric ozone.

In order to contribute to solving this problem, the present invention proposes to replace the F113-based compositions by a new composition based on methylene chloride and 1,1,1,3,3-pentafluorobutane. The latter compound, known in the profession under the name F365-mfc, has no destructive effect with respect to ozone (ODP=0).

DESCRIPTION OF THE INVENTION

The composition to be used according to the invention comprises from 30 to 70% by weight F365-mfc and from 70 to 30% methylene chloride. In this field, there exists an azeotrope whose boiling temperature is 33.6° C. at normal atmospheric pressure (1.013 bar) and the composition according to the invention has a pseudoazeotropic behaviour, that is to say the composition of the vapor and liquid phases is substantially the same, which is particularly advantageous for the applications envisaged. Preferably, the F365-mfc content is chosen between 50 and 60% by weight and that of methylene chloride between 50 and 40% by weight.

The composition according to the invention additionally has the significant advantage of not exhibiting an ignition point under the standard determination conditions (ASTM standard D-3828); the composition is thus nonflammable.

The F365-mfc/methylene chloride azeotrope is a positive azeotrope since its boiling point (33.6° C.) is less than those of the two constituents (F365-mfc: 40° C.; methylene chloride: 40° C.).

As in the known F113-based compositions, the composition according to the invention can advantageously be stabilized against hydrolysis and/or free-radical attacks which are capable of taking place in the cleaning processes by adding thereto a conventional stabilizing agent such as, for example, a nitroalkane, an epoxide or a mixture of such compounds, it being possible for the proportion of stabilizing agent to range from 0.01 to 5% with respect to the total F365-mfc + methylene chloride weight.

The composition according to the invention can be used in the same applications and according to the same techniques as the prior F113-based compositions.

EXAMPLES

The following examples illustrate the invention without limiting it.

EXAMPLE 1: DISCLOSURE OF THE AZEOTROPE 100 g of methylene chloride and 100 g of F365-mfc are introduced into the distillation flask of a distillation column (30 plates). The mixture is then put on total reflux for one hour to bring the system to equilibrium. At the temperature plateau (33.6° C.), a fraction (approximately 50 g) is withdrawn and analyzed by gas phase chromatography.

Examination of the results, recorded in the table below, indicates the presence of a F365-mfc/methylene chloride azeotrope.

|  | COMPOSITION (% BY WEIGHT) | |
|---|---|---|
|  | F365-mfc | $CH_2Cl_2$ |
| Initial mixture | 50 | 50 |
| Withdrawn fraction | 56.6 | 43.4 |

EXAMPLE 2: VERIFICATION OF THE AZEOTROPIC COMPOSITION 200 g of a mixture comprising 56.6% by weight F365-mfc and 43.4% by weight methylene chloride are introduced into the distillation flask of an adiabatic distillation column (30 plates). The mixture is then brought to reflux for one hour to bring the system to equilibrium, then a fraction of approximately 50 g is drawn off and analysed, as are the distillation bottoms, by gas phase chromatography. The results recorded in the following table show the presence of a positive azeotrope since its boiling point is less than those of the two pure constituents: F365-mfc and methylene chloride.

|  | COMPOSITION (% by weight) | |
|---|---|---|
|  | F365-mfc | $CH_2Cl_2$ |
| Initial mixture | 56.6 | 43.4 |
| Withdrawn fraction | 56.6 | 43.4 |
| Distillation bottoms | 56.6 | 43.4 |

Boiling temperature corrected for 1.013 bar: 33.6° C.

This azeotrope, used for the cleaning of solder flux or in the degreasing of mechanical components, gives results which are as good as those given by the compositions based on F113 and methanol.

EXAMPLE 3: COMPOSITION STABILISED BY NITROMETHANE 150 g of a mixture containing, by weight, 56.5% F365-mfc, 43.4% methylene chloride and 0.1% nitromethane as stabilizing agent are introduced into an ultrasound cleaning vessel. After the system has been put on reflux for one hour, an aliquot of the vapour phase is withdrawn. Its analysis by gas phase chromatography shows the presence of nitromethane, which indicates that the mixture is stabilized in the vapor phase.

|  | COMPOSITION (% by weight) | | |
| --- | --- | --- | --- |
|  | F365-mfc | $CH_2Cl_2$ | $CH_3NO_2$ |
| Initial mixture | 56.6 | 43.4 | 0.1 |
| Vapor phase | 56.49 | 43.49 | 0.02 |

EXAMPLE 4: COMPOSITION STABILISED BY PROPYLENE OXIDE

If Example 3 is repeated, replacing nitromethane by propylene oxide, the following results are obtained:

|  | COMPOSITION (% by weight) | | |
| --- | --- | --- | --- |
|  | F365-mfc | $CH_2Cl_2$ | $C_3H_6O$ |
| Initial mixture | 56.5 | 43.4 | 0.1 |
| Vapor phase | 56.49 | 43.49 | 0.02 |

EXAMPLE 5: CLEANING OF SOLDER FLUX 200 g of the F365-mfc/methylene chloride azeotropic composition are introduced into an Annemasse ultrasound vessel, and then the mixture is brought to boiling temperature.

Standard circuits (IPC-B-25 model), coated with solder flux and annealed in an oven for 30 seconds at 220° C., are immersed for 3 minutes in the liquid at boiling point under ultrasound, and then rinsed in the vapor phase for 3 minutes.

After drying in air, viewing in oblique light shows the complete absence of solder flux residue.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. An azeotropic composition or a composition which has about the same composition in vapor phase as in liquid phase when employed at reflux, consisting essentially of, on a weight basis, from 30 to 70% 1,1,1,3,3-pentafluorobutane and from 70 to 30% methylene chloride and optionally an effective amount of at least one stabilizer, said composition boiling at about 33.6° C. at normal atmospheric pressure.

2. Composition according to claim 1, consisting essentially of, by weight, from about 50 to about 60% 1,1,1,3,3-pentafluorobutane and from about 40 to about 50% methylene chloride.

3. Composition according to claim 1, wherein the stabilizing agent is a nitroalkane, an epoxide or a mixture of such compounds.

4. Composition according to claim 1, wherein the proportion of stabilizing agent is from 0.01 to 5% with respect to the total weight of 1,1,1,3,3-pentafluorobutane and methylene chloride.

5. Method for cleaning or drying a solid surface comprising applying an effective amount of a composition according to claim 1 to the solid surface.

6. Method of removing flux from a printed circuit comprising applying an effective amount of a composition according to claim 1 to the printed circuit.

7. Method of removing grease from a mechanical component comprising applying an effective amount of a composition according to claim 1 to the mechanical component.

8. An azeotrope, consisting essentially of, on a weight basis, about 56.6% 1,1,1,3,3-pentafluorobutane and about 43.4% methylene chloride boiling at about 33.6° C. at normal atmospheric pressure.

* * * * *